United States Patent [19]

Miller et al.

[11] 4,171,454

[45] Oct. 16, 1979

[54] OXIDATION PROCESS UTILIZING AMPHORA CATALYSTS

[75] Inventors: Arthur F. Miller, Cleveland; James L. Callahan, Wooster; Wilfrid G. Shaw, Lyndhurst, all of Ohio

[73] Assignee: The Standard Oil Company, Cleveland, Ohio

[21] Appl. No.: 566,782

[22] Filed: Apr. 10, 1975

Related U.S. Application Data

[63] Continuation-in-part of Ser. No. 490,429, Jul. 22, 1974, Pat. No. 3,966,639, which is a continuation-in-part of Ser. No. 271,837, Jul. 13, 1972, Pat. No. 3,848,033.

[51] Int. Cl.$^2$ .................. C07C 45/04; C07C 51/32; C07C 57/04
[52] U.S. Cl. ............................ 562/546; 252/432; 252/435; 252/437; 252/455 R; 252/456; 252/461; 252/462; 252/464; 252/467; 252/470; 252/471; 252/472; 252/477 R; 260/604 R; 562/547

[58] Field of Search .............. 260/533 N, 604 R; 252/477 R, 435, 437; 562/546, 547

[56] References Cited

U.S. PATENT DOCUMENTS

| | | | |
|---|---|---|---|
| 3,200,081 | 8/1965 | Callahan et al. | 260/533 N |
| 3,264,225 | 7/1966 | Callahan et al. | 260/533 N |
| 3,328,215 | 6/1967 | Johnson | 260/533 N |
| 3,338,952 | 8/1967 | Callahan et al. | 260/533 N |
| 3,798,176 | 3/1974 | Ao | 260/533 N |

*Primary Examiner*—Vivian Garner
*Attorney, Agent, or Firm*—John E. Miller, Jr.; Herbert D. Knudsen; Larry W. Evans

[57] ABSTRACT

Catalysts having a substantially spherical shape, a void center and a hole in the external surface communicating to the void center have been found to be especially effective in the oxidation of monoolefins to the corresponding unsaturated oxygenated compounds.

10 Claims, 1 Drawing Figure

U.S. Patent  Oct. 16, 1979  4,171,454
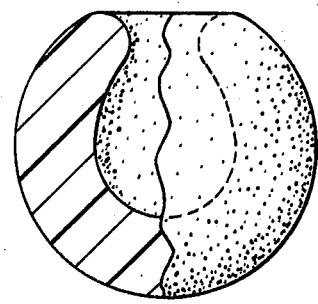

OXIDATION PROCESS UTILIZING AMPHORA CATALYSTS

CROSS REFERENCE TO RELATED APPLICATION

This patent application is a continuation-in-part of patent application Ser. No. 490,429, filed July 22, 1974, now U.S. Pat. No. 3,966,639, which is a continuation-in-part of Ser. No. 276,837, filed July 13, 1972, now U.S. Pat. No. 3,848,033, issued Nov. 12, 1974.

BACKGROUND OF THE INVENTION

The oxidation of olefinically unsaturated hydrocarbons to the corresponding unsaturated aldehydes and unsaturated acids by the reaction of a monoolefin with a molecular oxygen-containing gas in the presence of a supported metal oxide catalyst is well known. For example, U.S. Pat. No. 3,859,358 shows a vapor phase oxidation process utilizing catalysts comprising the oxides of uranium and molybdenum in the pelleted or small particulate form. Similarly, U.S. Pat. Nos. 2,941,007, 3,328,315, 3,338,952 and 3,200,081 disclose vapor phase oxidation processes utilizing catalysts of bismuth molybdate and bismuth phosphomolybdate, and antimony oxide in combination with oxides of uranium, iron, or manganese, these catalysts also being in pelleted or "fluidized" form.

The amphora form of a catalyst is clearly described by Callahan, Miller and Shaw in U.S. Pat. No. 3,848,033. The techniques employed in this patent are directly applicable to the production of amphora shaped oxidation catalysts utilized in the present invention.

SUMMARY OF THE INVENTION

This invention relates to the production of acrolein and acrylic acid from propylene, and methacrolein and methacrylic acid from isobutylene by reaction of the respective olefins with oxygen in the presence of an oxidation catalyst at an elevated temperature, the improvement comprising using as at least part of the catalyst an amphora catalyst having a substantially spherical shape, a void center and a hole in the external surface of the catalyst communicating to the void center.

Use of amphora shaped catalysts gives significant advantages in the areas of substantial conversion of the olefin to unsaturated carboxylic acid and high conversion to useful products.

DESCRIPTION OF THE DRAWING

The amphora form of the catalyst is shown in the FIGURE. It is seen that the catalyst from the outside looks like a sphere with a hole in it. From the cut-away section, it is seen that the interior of the sphere is void and that the hole in the external surface of the sphere communicates to this center void.

DETAILED DESCRIPTION OF THE INVENTION

The novel feature of the invention resides in the catalyst form. This amphora catalyst form can be made from any catalyst used in oxidation reactions by applying the techniques disclosed in U.S. Pat. No. 3,848,033. Broadly, these preparations involve dropping droplets of a slurry onto a particle bed to form the amphora.

When the droplet contacts the particle bed, it is, of course, spherical. Generally, the nature of the particle bed or the conditions of the particle bed, including heat or other sources of drying, are adjusted to dry the particles. It is hypothesized that one possible way the unique amphora can be formed is by removing the suspending liquid of the slurry, so that most, but not all, of the external surface becomes set. The suspended particles in the slurry then migrate to this set outer surface, and a void center is formed. In a similar manner, the portion of the external surface of the spherical droplet that was not originally dried migrates to the interior of the droplet. This migration "pulls" a hole from the external surface of the droplet to the void center.

The amphora shape can be obtained using a wide range of slurries and particle beds. A hydrophobic or hydrophilic particle bed can be employed to prepare the amphora. The specific technique may vary to some extent as different slurries and particles beds are employed, but the amphora is believed to be made in each case as described above. The amphora made by this process may have any size, but amphora having a diameter of 1 to about 10 mm. are normally used.

The oxidation process in which the amphora are used is substantially the same using the amphora shaped catalyst even though improved results are obtained by the use of the amphora. The catalyst compositions may be any of the catalysts employed in the art. These are normally catalysts such as those containing at least the oxides of bismuth and molybdenum. Preferably the oxidation catalysts in the present invention have the formula:

$$A_a D_b Fe_c Bi_d E_e Mo_f O_x$$

wherein
  A is an alkali metal, alkaline earth metal, Tl, In, rare earth metal or mixture thereof,
  D is Ni, Co, Mg, Mn or a mixture thereof; and
  E is phosphorus, arsenic, boron, chromium, tungsten or antimony,
and wherein
  a and e are independently 0–3,
  b is 0 to 20,
  c and d are independently 0.1 to 10,
  f is about 8 to about 16 and
  x is the number of oxygens required to satisfy the valence requirements of the other elements present.

Also particularly suitable catalysts for this process are those containing antimony oxide in combination with one or more of the metal oxides selected from the group consisting of uranium, iron, thorium, cerium, manganese or tin, wherein the atomic ratio of antimony to the second metal is in the range of from about 1:50 to about 99:1 as disclosed in U.S. Pat. Nos. 3,197,419, 3,198,750, 3,200,081, 3,200,084 and 3,264,225.

These oxide catalysts are normally supported on carriers such as $SiO_2$, $Al_2O_3$, $SiO_2$-$Al_2O_3$, $TiO_2$, $ZrO_2$, kieselguhr, montmorillonite, $AlPO_4$, $CaAl_2O_4$, $BPO_4$ and the like. Preferably at least 10% up to about 90% of the supporting compound by weight of the entire composition is employed.

The olefins undergoing oxidation in this invention are low molecular weight olefins such as propylene or isobutylene which are readily converted to the corresponding unsaturated aldehydes and acids by this process. The reaction may be conducted by contacting a mixture of olefin and an oxygen-containing gas with the catalyst at an elevated temperature, at atmospheric, superatmospheric or subatmospheric pressure.

The process conditions and reaction parameters for this reaction are well known. Broadly the molar ratio of oxygen to the olefin in the feed to the reaction vessel should be in the range of 0.5:1 to 5:1, with a ratio of about 1:1 to 2:1 being preferred. In many cases water in the mixture fed to the reaction vessel improves the selectivity of the reaction and yield of aldehyde and acid.

The reaction is carried out at a temperature within the range from about 200° to about 600° C. The preferred temperature range is from about 300° C. to about 500° C. The apparent contact time is not critical, and contact times in the range of from 0.1 to about 50 seconds may be employed.

The process is normally conducted in a fixed bed reactor, but use of a fluid bed reactor is possible with small amphora. With the use of the amphora catalyst in this process very desirable results are obtained. The amount of amphora shaped catalyst that can be employed may vary widely. The oxidation catalyst can be essentially all amphora, but can contain as little as about 5% by volume of the catalyst in the amphora shape. Normally, however, the oxidation catalyst contains more than 25% by volume of the catalyst in the amphora form.

SPECIFIC EMBODIMENTS

Comparative Examples A-C and Examples 1-3

Comparison of Tablets with Amphora in the Oxidation of Propylene

An oxidation catalyst having the formula 82.5%-$Co_{4.5}Ni_{2.5}Fe_3K_{0.07}BiP_{0.5}Mo_{12}O_{50.3}$-17.5% $SiO_2$ was prepared as follows:

4016 Grams of ammonium heptamolybdate, $[(NH_4)_6Mo_7O_{24}.4H_2O]$ were added to 8907 grams of water with stirring. To this solution were added 109 grams of phosphoric acid and 555 grams of Aerosil silica sol, and the resulting slurry was stirred until the contents were well dispersed. To this slurry the following solutions were added in the sequence given:

2482.5 grams of $Co(NO_3)_2.6H_2O$ and 1378 grams of $Ni(NO_3)_3.6H_2O$ dissolved in 6325 grams of water at 50°-60° C.;

2297 grams of $Fe(NO_3)_3.9H_2O$ dissolved in 422 grams of water at 50°-60° C.;

919.5 grams of $Bi(NO_3)_3.5H_2O$ dissolved in a mixture of 717 grams of water and 91.2 grams of nitric acid at 60°-75° C.;

17.1 grams of $KNO_3$ dissolved in 40 cc. of water. An additional 555 grams of Aerosil silica sol were then added and the entire mixture was stirred for an additional 30-45 minutes.

The catalyst slurry was spray dried and partially denitrified by a programmed heat treatment to remove 70-75% of the removable nitrates.

Tablet Preparation

Tablets representing the art and used in Comparative Examples A-C below were prepared as follows:

One percent graphite was added to the partially denitrified catalyst powder prepared above and the powder was then tabletted. The tablets having the dimensions of 5 mm.×2.8 mm. were further heat treated to remove the remaining nitrates and were then calcined at 550° C. for five hours.

Amphora Preparation

Amphora formed catalyst representing the invention and used in Examples 1-3 below were prepared as follows:

To 190 grams of water were added 350 grams of the partially denitrified catalyst powder of Example A. After thorough mixing, the slurry was blended in a blender for 3 minutes. The slurry was then allowed to age for several hours. Then 10-12 mls. of additional water was added and reblended for approximately 10 seconds. The slurry was then dropped onto a bed of warm calcined powder of the same composition as the final amphora catalyst, and heated gently under a heat lamp and a warm air stream to dry the amphora. The amphora catalyst was then heat treated to remove the remaining nitrates and then calcined for five hours at 550° C. The amphora had diameters of approximately 3 mm.

Oxidation

The catalysts prepared above were compared in the oxidation reaction of propylene to acrolein and acrylic acid. A fixed-bed stainless steel reactor was utilized having a 1.27 cm. O.D. and a reaction zone of 20 cc. capacity. The propylene and air feeds were premixed in the desired ratios in a preheated mixing coil which led to the single reactor inlet. The reactions were conducted through the reaction zone under atmospheric pressure, using a molar ratio of propylene:air:water equal to 1:11:4, respectively, and a contact time of 2.7 seconds. The tabletted and the amphora forms of the catalyst are directly compared in the Table at three different reaction temperatures. Percent per pass conversion to acrolein, percent per pass conversion to acrylic acid and percent useful conversion as reported in the Table are defined as follows:

$$\% \text{ Per Pass Conversion to Acrolein} = \frac{\text{Grams of carbon in Acrolein Obtained}}{\text{Grams of Carbon in Propylene fed}} \times 100$$

$$\% \text{ Per Pass Conversion to Acrylic Acid} = \frac{\text{Grams of Carbon in Acrylic Acid Obtained}}{\text{Grams of Carbon in Propylene Fed}} \times 100$$

% Useful Products = Sum of % Per Pass Conversion to Acrylic Acid and Acrolein $$\% \text{ Total Conversion} = \frac{\text{Grams of Carbon in Propylene Converted}}{\text{Grams of Carbon in Propylene Fed}} \times 100$$

Table I

Comparison of Amphora and Tabletted form of Oxidation Catalyst for the Conversion of Propylene to Acrolein and Acrylic Acid

| Example | Catalyst Form | Reaction Temp., °C. | Results, % Per Pass Conv. to Acrylic acid | Per Pass Conv. to Acrolein | Useful Products | Total Conversion |
|---|---|---|---|---|---|---|
| Comp A | Tablet | 310 | 4.8 | 74.8 | 79.6 | 81.7 |
| 1 | Amphora | 310 | 7.1 | 84.3 | 91.4 | 93.9 |
| Comp B | Tablet | 328 | 7.7 | 82.6 | 90.3 | 92.9 |
| 2 | Amphora | 328 | 10.8 | 83.1 | 93.9 | 96.8 |
| Comp C | Tablet | 338 | 8.8 | 82.0 | 90.8 | 93.6 |
| 3 | Amphora | 338 | 13.1 | 82.6 | 95.7 | 99.5 |

It can be observed from the Table that the amphora form of the catalyst is more active at a given temperature. The amphora form also gives essentially one and a half times the conversion to acrylic acid than is obtained with the tabletted form as well as the same or greater conversion to acrolein. These advantages are particularly pronounced at the lower reaction temperatures (310° C.). Since acrylic acid is the ultimate product desired, it is an important advantage to obtain a high conversion to the acid at this stage of the oxidation. It is further observed that the conversion to useful products obtained with the use of the amphora catalyst is markedly improved over that obtained with the tabletted form.

We claim:

1. In the process for the oxidation of propylene and isobutylene to the corresponding unsaturated aldehydes and unsaturated acids by the vapor phase reaction of the olefin with oxygen in the presence of an oxidation catalyst at an elevated temperature, the improvement comprising:

using as at least part of the catalyst an amphora catalyst having a substantially spherical shape, a void center and a single hole in the external surface of the catalyst communicating to the void center.

2. The process of claim 1 wherein the amphora catalyst contains at least the oxides of bismuth and molybdenum.

3. The process in claim 2 wherein the amphora catalyst contains at least the oxides of bismuth, molybdenum and iron.

4. The process in claim 3 wherein the amphora catalyst has the composition $Co_{4.5}Ni_{2.5}Fe_3K_{0.07}BiP_{0.5}Mo_{12}O_{50.3}$ and the reaction is conducted at 310° C.

5. The process in claim 1 wherein the amphora catalyst composition is supported on a carrier selected from the group consisting of silica, alumina and silica-alumina.

6. The process in claim 1 wherein the amphora catalyst contains antimony oxide in combination with one or more of the metal oxides selected from the group consisting of uranium, iron, thorium, cerium, manganese and tin.

7. The process in claim 6 wherein the amphora catalyst contains the oxides of antimony and uranium.

8. The process in claim 6 wherein the amphora catalyst contains the oxides of antimony and iron.

9. The process of claim 1 wherein more than 25% of the catalyst is the amphora catalyst.

10. The process of claim 1 wherein essentially all of the catalyst is the amphora catalyst.

* * * * *